United States Patent
Weber et al.

(10) Patent No.: US 10,488,315 B2
(45) Date of Patent: Nov. 26, 2019

(54) METHODS AND SYSTEMS FOR PREDICTION OF SENSOR RESPONSE TIME

(71) Applicant: Ford Global Technologies, LLC, Dearborn, MI (US)

(72) Inventors: David Charles Weber, Toledo, OH (US); Garry Anthony Zawacki, Livonia, MI (US); Vidhushekhar Vasant Zambare, Novi, MI (US); Evangelos P. Skoures, Detroit, MI (US); Zaid Alnaqash, Farmington Hills, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 684 days.

(21) Appl. No.: 15/042,767

(22) Filed: Feb. 12, 2016

(65) Prior Publication Data

US 2017/0234786 A1  Aug. 17, 2017

(51) Int. Cl.
*G01N 15/06* (2006.01)
*G01M 15/10* (2006.01)
*G01N 15/00* (2006.01)

(52) U.S. Cl.
CPC ...... *G01N 15/0656* (2013.01); *G01M 15/102* (2013.01); *F01N 2560/05* (2013.01); *G01N 2015/0046* (2013.01)

(58) Field of Classification Search
CPC ............. F01N 2560/05; F01N 2560/20; F01N 2550/04; F01N 3/023; F01N 9/002; F01N 2260/04; G01N 15/0656; G01N 2015/0046; G01M 15/102
See application file for complete search history.

(56) References Cited

U.S. PATENT DOCUMENTS

| | | | |
|---|---|---|---|
| 8,036,814 B2 | 10/2011 | Weber et al. | |
| 8,161,738 B2* | 4/2012 | He | F01N 3/0253 60/286 |
| 9,032,719 B2 | 5/2015 | Sun, Jr. et al. | |
| 2007/0125075 A1* | 6/2007 | Zanini-Fisher | F01N 11/00 60/297 |
| 2010/0089041 A1* | 4/2010 | Tai | F01N 9/002 60/287 |
| 2012/0117945 A1* | 5/2012 | Krafthefer | F01N 11/00 60/274 |
| 2012/0125081 A1* | 5/2012 | Yadav | F01N 11/00 73/23.33 |

(Continued)

OTHER PUBLICATIONS

Barrs et al, "Particulate matter sensor for on-board diagnosis (OBD) of diesel particulate filters", 14th ETH Conference on Combustion Generated Nanoparticles Zürich, Aug. 3, 2010.*

*Primary Examiner* — Mohamed Charioui
*Assistant Examiner* — Catherine T. Rastovski
(74) *Attorney, Agent, or Firm* — Geoffrey Brumbaugh; McCoy Russell LLP

(57) ABSTRACT

Methods and systems are provided for predicting response time of a particulate matter (PM) sensor and resetting the PM sensor upon completion of response time prediction, independent of actual or predicted soot load on PM sensor. Soot accumulation data collected during steady state vehicle operation may be fitted with a time-based polynomial function and sensor output and regeneration schedule may be estimated from the curve fit even if the overall signal is noisy.

18 Claims, 5 Drawing Sheets

(56) References Cited

U.S. PATENT DOCUMENTS

2012/0144813 A1\* 6/2012 Yahata ................ F01N 11/007
  60/311
2015/0168285 A1\* 6/2015 Hedayat ............. G01M 15/102
  73/23.33

\* cited by examiner

METHODS AND SYSTEMS FOR PREDICTION OF SENSOR RESPONSE TIME

FIELD

The present description relates generally to methods and systems for predicting response time of a particulate matter (PM) sensor.

BACKGROUND/SUMMARY

Engine combustion may generate particulate matter (PM) and pollutants such as soot and aerosols that can be exhausted to the atmosphere. Various technologies have been developed for filtering such PMs before the exhaust is released to the atmosphere. As an example, to improve emissions compliance, particulate filters (PFs) may be included in the engine exhaust system. One or more PM sensors (also known as soot sensors) may be located upstream and/or downstream of a particulate filter (PF), and may be used to sense PM loading on the filter, schedule regeneration of the filter, and/or diagnose the functionality of the filter.

When included, PM sensors may be used to sense concentration and/or flux of PM entrained in the exhaust gas based on a correlation between a measured change in electrical current and/or conductance at a sensor element and the amount of PM deposited on the element (such as between a pair of measuring electrodes). As such, PM sensors need to be periodically regenerated and reset once the soot accumulation signal strength reaches a threshold value. The time required for a sensor signal to reach the threshold value after which the sensor may be regenerated and reset is known as the response time of the sensor. This response time is inversely proportional to the PM concentration in the exhaust gas. In order to meet emissions regulations, PM sensors are required to be intermittently regenerated and reset (e.g., at least once within each emission test cycle). In addition, to meet emission standards, it may be desirable for an engine controller to have collected a maximum number of sensor response time signals per drive cycle (e.g., at least 4 per 18 mins for a federal test procedure cycle).

One example approach shown by Min Sun in U.S. Pat. No. 9,032,719 discloses a method to reset a PM sensor based on soot accumulation. Therein, PM sensor current may increase with the deposition of soot on the sensor. After a period of time (known as the response time for the sensor), the PM sensor current may reaches a threshold value correlating with the soot load on the sensor reaching a threshold load. At this time, the PM sensor is regenerated and reset.

However, the inventors have recognized that PM sensors may be prone to contamination from impingement of larger particulates present in the exhaust gases and/or water droplets, thus affecting the PM sensor sensitivity and leading to errors in electrical current measurement and PM sensor regeneration. Such erroneous data may not reflect the actual soot concentration in the exhaust gas and hence should not be utilized for determination of sensor response time and particulate filter efficiency. Due to repeated occurrence of noise, a large amount of data may not be utilized for PM sensor operation and is required to be discarded. In the absence of an actual response time, the soot concentration calculation from an average response time may have reduced accuracy. For short drives, there may be not be sufficient measurement of soot concentration due to the lack of time in the given drive cycle. As such, this reduces the accuracy of the soot monitoring system. For example, for a soot sensor downstream of the particulate filter, if the average response time is higher than the actual response time, soot will be underestimated thereby potentially failing to detect leakage of soot past a defective filter into the exhaust flow, and adversely affecting emissions quality. Also, degradation of the filter (e.g., due to high soot leakage) may not be detected. In addition, by discarding a large amount of data, it may become difficult to meet the requirement of completing on-board diagnostics and meeting a target completion ratio within a given drive cycle.

The inventors herein have identified an approach by which the issues described above may be at least partly addressed. One example method includes collecting exhaust soot sensor data during engine operation while sensor noise is lower than a threshold; fitting a time-based curve to the collected data; predicting a sensor response time based on the curve fit; and in response to the curve fit being higher than a threshold, regenerating the soot sensor independent of a soot load of the sensor. In this way, a completion ratio of PM sensor diagnostics may be improved. Also, by using a predicted sensor output, soot concentration and/or soot flux in the exhaust may be estimated.

As an example, electric current signals corresponding to soot accumulation on a particulate matter (PM) sensor are collected over a period of time. In case of noisy PM sensor current signals (that is, on occurrence of a larger than threshold change in signal strength), the accumulated data is not used for determining an actual soot response time. The response time for regenerating the PM sensor (when soot load accumulated on the sensor reaches a threshold), may be predicted from at least a part of the accumulated signal. The actual response time may correspond to a duration of time elapsed between the end of one regeneration event and the start of an immediately subsequent regeneration event of the PM sensor (with no other regeneration event in between). As such, during steady-state driving conditions, the PM sensor signal may be less noisy, and the propensity for sensor noise may be higher during vehicle transients. Therefore, at least a portion of the total signal accumulated during steady-state conditions may be used for prediction of a response time of the sensor. As such, the prediction may be performed even before the accumulated signal reaches a pre-determined regeneration threshold and the sensor concentration measurements may be made early. A polynomial (quadratic) equation may be used to fit a plot generated from the data accumulated during the steady-state conditions. The response time may be predicted by extrapolating the curve fitted to the accumulation plot even before the actual signal reaches the threshold value. In addition, the linear term of the quadratic fit may be used to estimate the soot concentration on the PM sensor, which is also used to predict the time required (response time) for the soot level to reach the threshold value. The quality of the quadratic fit may be estimated by comparing the coefficient of determination ($R^2$) of the plot to a threshold, and if the $R^2$ value is higher than the threshold (that is, the fit is sufficiently reliable), sensor response time may be predicted by extrapolating the quadratic fit to the accumulation plot and stored. The predicted response time may be used to update the average response time of the PM sensor. Once sufficient data has been accumulated to enable a reliable prediction of response time, the PM sensor may be immediately regenerated and collection of a new dataset may be restarted. In particular, the sensor may be regenerated independent of the actual and/or predicted response time. If the $R^2$ value is lower than the threshold (i.e. the fit is unreliable), and if the response time is very long or very short, the dataset may be discarded. The PM sensor may then be regenerated and reset to start another round of accumulation at a pre-determined response time. The predetermined response time may be based on the average response time, or based on a duration elapsed since a last regeneration of the sensor.

In this way, by relying on signal accumulated during conditions when sensor noise is lower, such as during steady-state conditions, PM sensor soot concentration may be calculated and regeneration can be scheduled even if the overall sensor signal (e.g., over a drive cycle) is noisy. By predicting the response time of a PM sensor by applying a quadratic fit to a plot generated from soot sensor data accumulated during steady-state conditions, the accuracy of the response time used for PM sensor measurements may be improved. By using a larger portion of the accumulated signal for response time prediction (and discarding a smaller portion), diagnostics may be completed within a drive cycle without reducing an accuracy in the estimation of the response time. By predicting response time and regenerating the PM sensor once sufficient data for enabling a reliable prediction is accumulated, a new dataset collection may commence without having to wait for the actual and/or predicted response time. As a result, a larger number of sensor response time signals may be collected per drive cycle, improving the completion ratio for the sensor. The technical effect of using a quadratic fit to the accumulation plot is that soot accumulation may also be estimated from the linear term of the fitted data. By estimating soot load on a sensor from the fit to soot accumulation plot using both techniques (that is, by extrapolating the quadratic fit to the accumulation plot and by using the linear term of the same fit), it may be possible to improve the accuracy of the average signal and thus the accuracy of the soot concentration measurement may be improved. For example, the response time learned via the first approach may be confirmed using the response time learned via the second approach. Also, a more accurate predicted response time may be used for sensor soot concentration measurement in place of an actual response time which may be not be accurate for the given drive cycle. By using a larger proportion of the accumulated signal for response time prediction, the likelihood of completing PM concentration measurement at least once within an emission test cycle (such as a federal test procedure cycle) is increased, improving engine emissions compliance. It will be appreciated that the method of predicting a sensor response time using a quadratic fit to a part of a signal accumulated at the sensor may be similarly utilized for a plurality of different sensors present in the vehicle.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 2:
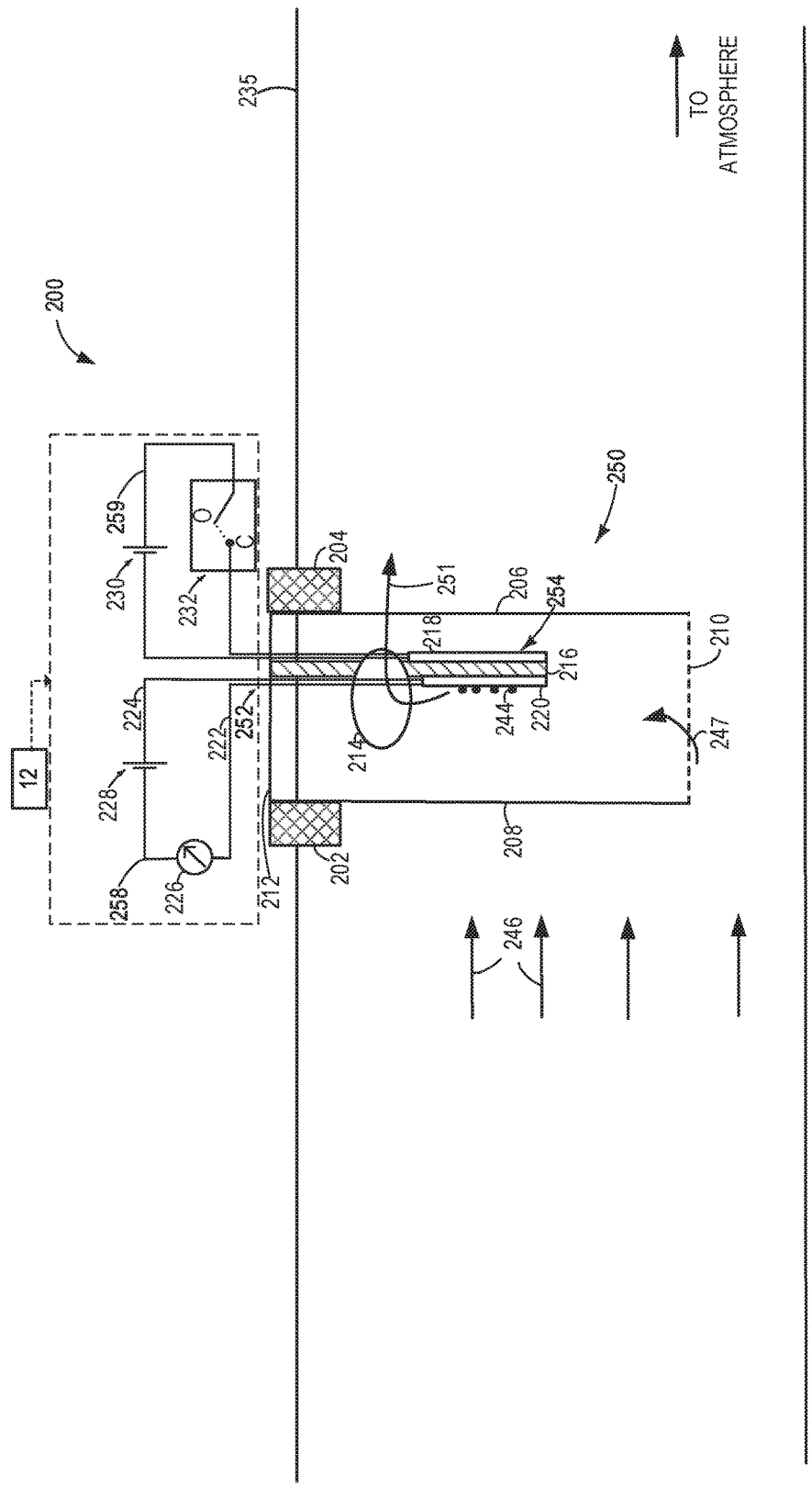
FIG. 2 shows an example embodiment of the PM sensor of FIG. 1.
Figure 3:
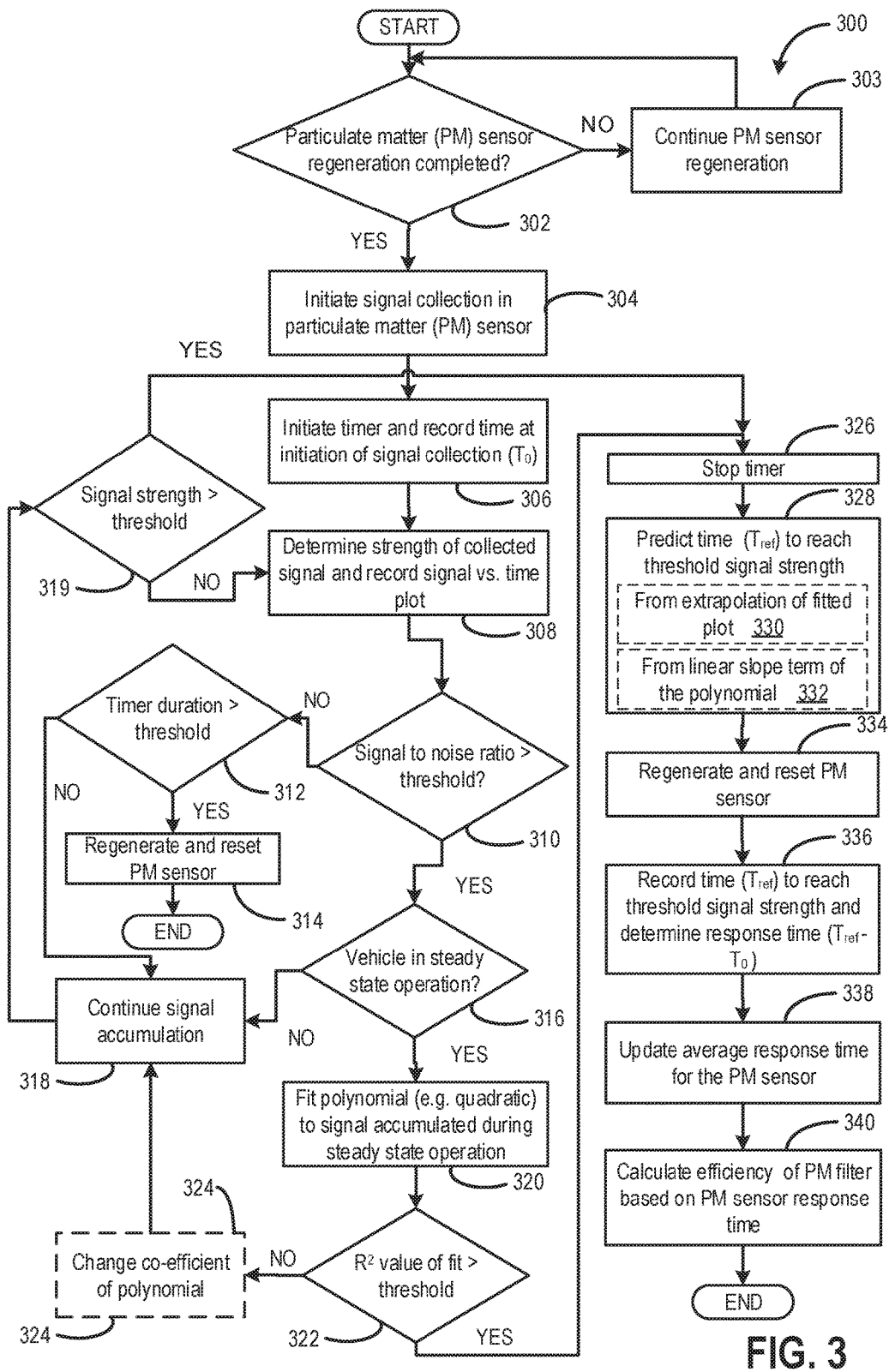
FIG. 3 shows a flow chart illustrating a method that may be implemented for predicting a response time of the PM sensor.
Figure 4:
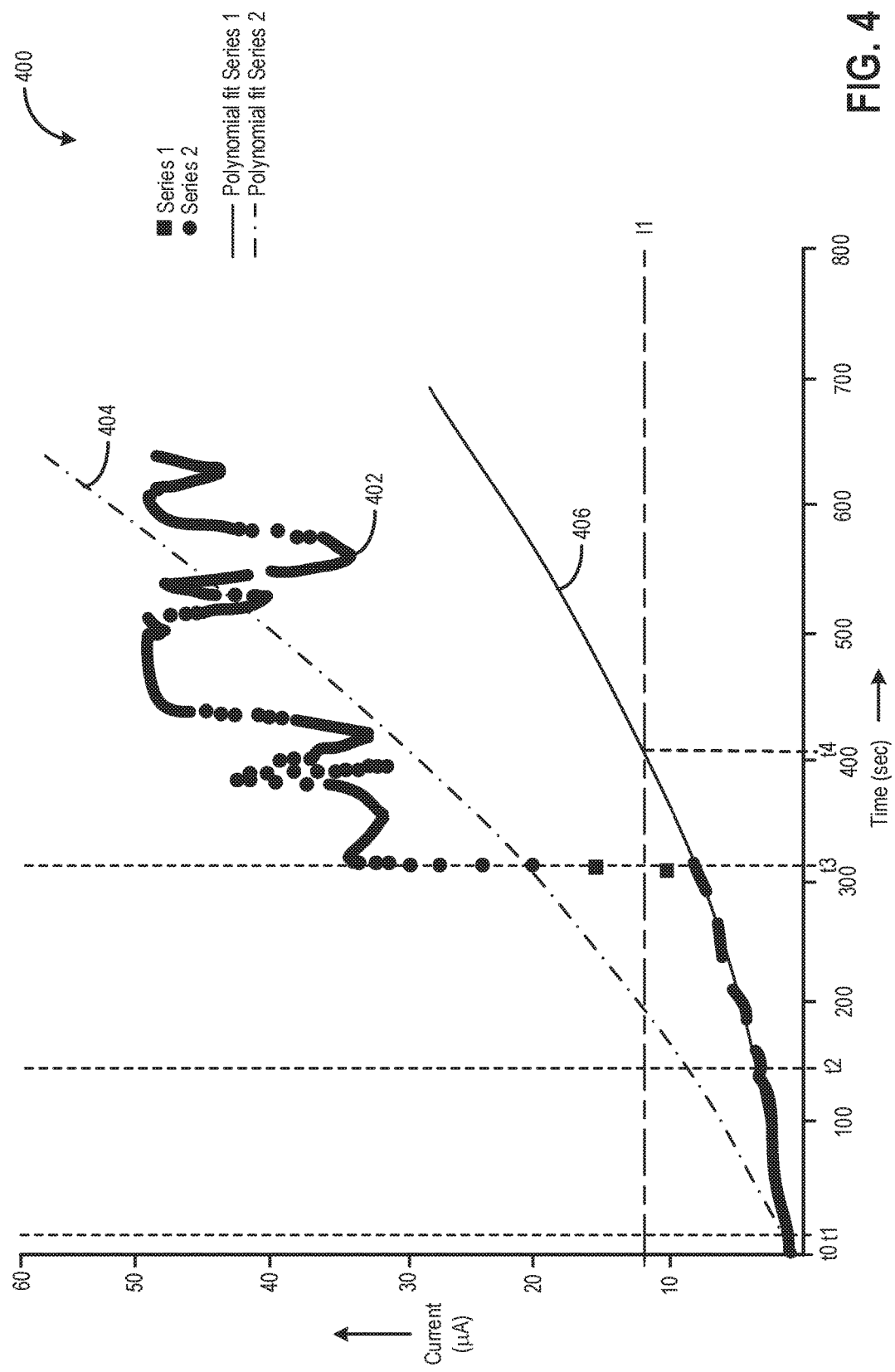
FIG. 4 shows an example fitting of a quadratic curve to PM sensor signals accumulated during steady-state engine operation.

The following description relates to systems and methods for predicting response time of a particulate matter (PM) sensor and resetting the PM sensor. In this example, the PM sensor is coupled to an engine system such as the engine system shown in FIG. 1. A PM sensor may be coupled to an exhaust passage upstream and/or downstream from a particulate matter filter. The PM sensor is used to measure the concentration and/or flux of conducting soot particles in any combustion exhaust due to the respiration hazard of PM in the air. A detailed description of the PM sensor coupled to the exhaust passage is shown in FIG. 2. One example of usage of the PM sensor in the automobile industry is to control or diagnose emission of regulated PM emission by the automobile. An engine controller is configured to perform a control routine, such as the example routine of FIG. 3, to predict a response time for the PM sensor based on soot accumulation signal obtained during steady-state driving conditions. As illustrated in FIG. 4, a quadratic curve may be fit to accumulated PM sensor signals and used for response time prediction. An example of PM sensor regeneration based on completion of response time prediction is shown in FIG. 4. In this way, PM sensor signal collected during steady-state vehicle operation may be used to predict the response time for the sensor and the average response time may be updated and a maximum number of sensor response time signals may be collected per drive cycle to meet federal standards.

Figure 1:
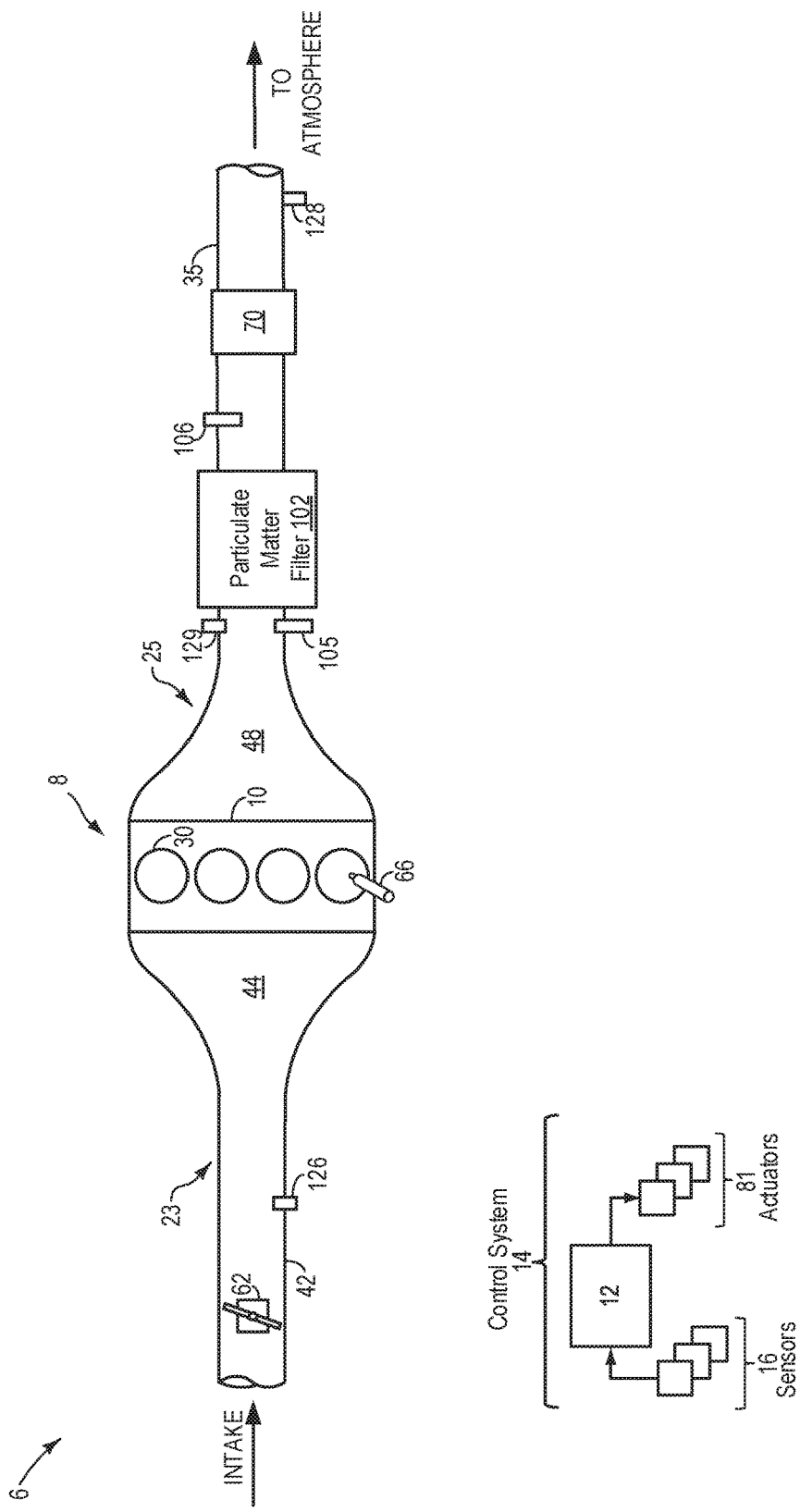
FIG. 1 shows a schematic diagram of an engine and an associated particulate matter (PM) sensor positioned in an exhaust flow.

FIG. 1 shows a schematic depiction of a vehicle system 6. The vehicle system 6 includes an engine system 8 and one possible case for a particulate matter (PM) sensor and system. The engine system 8 may include an engine 10 having a plurality of cylinders 30. Engine 10 includes an engine intake 23 and an engine exhaust 25. Engine intake 23 may optionally include a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Engine exhaust 25 may include one or more emission control devices 70, which may be mounted in a close-coupled position in the exhaust. One or more emission control devices may include a three-way catalyst, lean NOx trap, SCR catalyst, etc. Engine exhaust 25 may also include a particulate filter (PF) 102, which temporarily filters PMs from entering gases, positioned upstream and/or downstream of emission control device 70. PF 102 may have a structure made of, for example, porous cordierite or porous silicon carbide, with a plurality of channels inside for filtering particulate matter from diesel exhaust gas.

Tailpipe exhaust gas that has been filtered of PMs, following passage through PF 102, may be measured in a PM sensor 106 and further processed in emission control device 70 and expelled to the atmosphere via exhaust passage 35. In addition to the PM sensor 106, another PM sensor 105 may be coupled to the engine exhaust 25 upstream of the PF 102. In the depicted example, PM sensors 105 and 106 are resistive sensors that estimate the filtering efficiency of the PF 102 based on conductance measured across the sensor elements of the PM sensor. The measured conductance is used to calculate tailpipe PM emission and PF 102 efficiency. The PM sensor 105 may be used to measure soot concentration upstream of the PF 102 and improve the PF efficiency calculation and/or determine the PF soot load to allow scheduling PF regeneration. Alternatively, the PM sensor 105 may be solely used to calculate PM tailpipe emissions. A schematic view of the PM sensor(s) 105 and/or 106 is shown at FIG. 2, as described in further detail below.

The soot load escaping the PF 102 due to inefficiency of filtration of the particles may be deposited on the electrodes of the PM sensor 106. PM sensors need to be regenerated and reset in response to the soot accumulation signal strength reaching a predefined threshold value. The time required for the PM sensor signal to reach the threshold value is defined as the response time of the PM sensor. In one example, during transient engine operations and/or due to impingement of large soot particles or water droplets on sensor elements, the soot accumulation signal may be noisy (e.g., with intermittent spikes and/or dips in the signal) leading to erroneous estimation of PM sensor response time. During such circumstances, a part of the soot accumulation signal that is free of noise (such as signal accumulated during steady state operation of the vehicle) may be used to predict the PM sensor response time. The soot sensor data collected during the steady-state operation is collected on a common (same) drive cycle as the transient engine operation. Therefore the entire set of data collected within a drive cycle need not be discarded in the presence of any noisy signal. Once sufficient reliable data is accumulated and prediction of response time is complete, the PM sensor may be regenerated and reset even before reaching the actual and/or predicted response time and accumulation of a new dataset may begin. An example method describing the prediction of PM sensor response time using the data accumulated over the steady-state operation is discussed in relation to FIG. 3.

The vehicle system 6 may further include control system 14. Control system 14 is shown with a controller 12 receiving information from a plurality of sensors 16 (various examples of which are described herein) and the controller 12 sending control signals to a plurality of actuators 81 (various examples of which are described herein). As one example, sensors 16 may include flow rate sensor 126, exhaust gas sensors (located in exhaust manifold 48, including temperature sensor 128, pressure sensor 129, Oxygen sensor, NOx sensor, $NH_3$ sensor), and PM sensors 105 and 106. Other sensors such as additional pressure, temperature, air/fuel ratio, exhaust flow rate and composition sensors may be coupled to various locations in the vehicle system 6. As another example, the actuators may include fuel injectors 66, throttle 62, exhaust valves and PM sensor controls that control filter regeneration (not shown) of the PF and the PM sensor respectively, etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller. An example routine is described herein with reference to FIG. 3. FIG. 3 applies to any control of a PM sensor, whether the soot is from engine exhaust or any other source.

FIG. 2 shows a schematic view of an example embodiment of a particulate matter (PM) sensor 200. In one example the PM sensor 200 may be one of the PM sensor(s) 105 and 106 in FIG. 1. The PM sensor 200 may be configured to measure PM mass, PM flux and/or concentration in the exhaust gas, and as such, may be coupled to an exhaust passage (e.g., such as the exhaust passage 35 shown in FIG. 1), upstream and/or downstream of a particulate filter (such as PF 102 shown in FIG. 1).

As shown in FIG. 2, the PM sensor 200 is disposed inside exhaust passage 235 with exhaust gases flowing from downstream of a diesel particulate filter towards an exhaust tailpipe, as indicated by arrows 246. In another example, the PM sensor 200 may be disposed inside exhaust passage 235 upstream of the particulate filter. PM sensor 200 includes a protection tube 250 that may serve to protect a PM sensor element 254 of the PM sensor 200 housed within and may additionally serve to redirect exhaust gas flow over the PM sensor element 254 as explained below.

The PM sensor element 254 includes a pair of interdigitated electrodes 220 forming a "comb" structure. These electrodes may be typically manufactured from metals or conductive ceramic such as platinum, gold, osmium, rhodium, iridium, ruthenium, aluminum, titanium, zirconium, and the like, as well as, oxides, cements, alloys and combination comprising at least one of the foregoing metals or conductive ceramics. The electrodes 220 are formed on a substrate 216 that is typically manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the pair of interdigitated electrodes. The spacing between the comb "tines" of the two electrodes may typically be in the range from 10 micrometers to 100 micrometers with the linewidth of each individual "tine" being about the same value, although the latter is not necessary. As shown in FIG. 2 (in side view), the interdigitated electrodes 220 extend along and cover a portion of the substrate 216.

A positive electrode of the pair of interdigitated electrodes 220 is connected with connecting wires 224 to a positive terminal of a voltage source 228 of a first electric circuit 258. A negative electrode of the pair of interdigitated electrodes 220 is connected to a measurement device 226 via a connecting wire 222, and further connected to a negative terminal of the voltage source 228 of the first circuit 258. The interconnecting wires 222 and 224, the voltage source 228 and the measurement device 226 are part of the first circuit 258 and are housed outside the exhaust passage 35 (as one example, <1 meter away). Further, the voltage source 228 and the measurement device of the circuit 258 may be controlled by a controller, such as controller 12 of FIG. 1. In one example, instead of the controller 12, a nearby dedicated controller connected by means of suitable wiring to the PM sensor 200 may be used to control the PM sensor 200 in order to avoid any stray conductance. Alternatively, the dedicated controller may be configured as a control module within controller 12. As such, the measurement device 226 may be any device capable of reading an electric current change across the electrodes, such as a microammeter. In another embodiment, device 226 may be a voltmeter, also capable of estimating change in resistance across the electrodes. As PM or soot particles get deposited between the electrodes 220, the resistance between the electrode pair may start to decrease, which is indicated by an increase in current measured by the measurement device 226. The controller 12 may be able to determine the current and infer a corresponding PM or soot load on the planar electrodes 220 of the PM sensor 200. By monitoring the load on the PM sensor electrodes 220 (on the element 254), the exhaust soot load (concentration of PM in the flowing exhaust gas 246) may be determined, and thereby used to diagnose and monitor the health and functioning of the PF. Further, the flux rate in mass per second, particles per second, mass per volume per second etc. may be measured.

The protection tube 250 may be a hollow cylindrical tube with an upstream tube wall 208 (e.g., upstream facing wall), a downstream tube wall 206 (e.g., downstream facing wall), and a top surface 212. The upstream tube wall 208 may be closer to a PF than the downstream tube wall 206 when positioned in an exhaust passage 235 where the PF is positioned upstream of the PM sensor (such as the PM sensor 106 in FIG. 1). Further, exhaust gases flowing through the exhaust passage 135 may first contact the upstream tube wall 208 of the PM sensor. The top surface 212 may further include an inset portion 252 through which the PM sensor element 254 and its accompanying electrical connections may be inserted into the protection tube 250 and mechanically held in place and is further sealed to protect the PM sensor element 254 housed within the PM sensor 200. The protection tube 250 may be mounted onto the exhaust passage 235 (exhaust passage 35 in FIG. 1) via sensor boss 202 and 204 such that the central axis of the protection tube 250 is along the Y-axis, and also such that the central axis of the protection tube 250 is generally perpendicular to the exhaust passage 35 and the exhaust flow through the exhaust passage. As shown in FIG. 2, the protection tube 250 extends into a portion of the exhaust passage 235. The depth to which the protection tube extends into the exhaust passage may depend on exhaust pipe diameter. In some examples, the protection tube may extend to about one third to two thirds of the exhaust pipe diameter. The bottom of the protection tube 250 (at 210) may be a straight line or may be cut at an angle forming an inlet that introduces exhaust flow into the PM sensor 200. The PM sensor 200 also includes an outlet 214 positioned a distance away from the inlet of the PM sensor 200. The outlet 214 may comprise of a single hole or plurality of holes positioned along one or more of a back wall and a front wall of the protection tube 250 (not shown) or there may be other means to direct flow out of the protection tube 250. As such, the front wall and the back wall of the protection tube 250 may be surfaces of the hollow cylindrical protection tube 250 that are different from the upstream tube wall 208 and the downstream tube wall 206. While the outlet 214 is shown as an elliptical hole in FIG. 2, other shapes and sizes of the outlet 214 may also be used without departing from the scope of this disclosure.

Incoming exhaust flow 246 (also called incoming exhaust or incoming exhaust gas) refers to exhaust upstream of the PM sensor 200, which enters the inlet 210 of the PM sensor 200. In one example, the exhaust flow 246 may be the exhaust gas that exits the PF (in case of PM sensor 106 in FIG. 1). In another example, the exhaust flow 246 may be the flow feeding the PF (in case of PM sensor 105 in FIG. 1). The exhaust flow 247 flowing into the inlet opening 210 flows into the protection tube 250 of the PM sensor 200. The exhaust flow 247 may include a portion or a representative sample (i.e. well mixed fraction) of the incoming exhaust flow 246. A set of particulates 244 present in the exhaust flow 247 may be subsequently deposited on the PM sensor element 254 and adhere to the electrodes 220 and the gap surface. Exhaust flow 251 may be a portion of the incoming exhaust 246 that exits the PM sensor electrode via the outlet 214.

When the set of particulates 244 are deposited on the PM sensor element 254, particularly on the electrode 220 edges and on the gap of the non-conductive sensor substrate 216, the current as measured in the first electric circuit 258 by the measurement device 226 increases due to conducting PM bridging the electrode gap. The controller 12 may compute a soot load on the PM sensor electrodes 220 based on the current measured by the measurement device 226. When the current reaches a threshold current, it may be inferred that the soot load has reached a threshold load. The time to reach this load and current will be mostly inversely proportional to either the soot concentration or the soot flux of the exhaust gas 246 and 247. At this time, the controller (controller 12 in FIG. 1) would store the time signal and calculate the PM value using other sensors (such as sensors 16 in FIG. 1). Also, at this time the substrate 216 and the electrodes 220 must be cleaned to restart PM accumulation. Therefore the PM sensor electrodes 220 may be regenerated to clean the electrode surface of any particulates deposited on them. Due to emissions regulations, PM sensors are usually required to obtain one initial cleaning and one response time measurement at least once within any given emission test cycle (such as a federal test procedure cycle, World Harmonized Transient Cycle, New European Driving Cycle etc.). The cycle varies worldwide based on the respective regulations of a country and/or regulatory agency. Therefore it is important to accurately measure PM sensor response time such that sensor regeneration may take place accurately.

The PM sensor element 254 also includes a heating element 218 that is integrated into the sensor substrate 216 such that the heat easily conducts to the electrodes 220. The heating element 218 may be coupled to the second electric circuit 259 and may comprise a temperature sensor, and a heater. Possible materials for the heater and the temperature sensor forming the heating element 218 may include platinum, gold, palladium, and the like; and conductive ceramics, alloys, oxides, and combinations comprising at least one of the foregoing materials, with platinum/alumina, platinum/palladium, platinum, and palladium. The heating element 218 may be used for regenerating (i.e. burning off the soot particles) the PM sensor element 254. Specifically, during conditions when the particulate matter load 244 or soot load of the PM sensor element 254 is higher than a threshold, an electric current may be circulated through the heating element 218 generating heat that may be used to burn off the accumulated soot particles 244 from the electrode surface of the sensor element 254. During PM sensor regeneration, the controller 12 may provide a current using an external voltage source 230 coupled to a second electric circuit 259, which is needed for operating the resistive heating element 218 (the resistance of which is R). The method includes heating the electrode 220 surface to a temperature high enough to burn the soot particles using oxygen gas in the exhaust. Especially the substrate 216 surface must be thoroughly cleaned. In addition, the controller 12 may close the switch 232 (coupled to the second electric circuit 259) for a pre-determined time (or using pulsed modulation techniques) to complete the second circuit 259 and to apply the current (I) via the voltage source 230 to the heating element 218 in order to raise the temperature of the heating element 218 (power delivered is $I^2R$). Alternatively, on passage of current through the heating element 218, the decrease in soot load on the sensor element may be estimated by monitoring a change in electric current (of the sensor 226), and in response to the electric current value reaching a threshold, the switch 223 may be actuated to the open position indicating completion of the sensor regeneration. In one example, the temperature of the electrode 220 surface may be measured by a sensor couple to an additional electric circuit similar to the circuits 258 and 259. The additional electric circuit may be beneficial to heater 218 control and electrode 220 soot conductivity measurement. The resistance of the heater 218 may be measured using a current sensor within circuit 259.

By regenerating and resetting the PM sensor 200, it may be returned to a condition (e.g., unloaded or only partially loaded condition) more suitable for collecting exhaust soot since the starting load of PM will be zero or will be a known amount. The time elapsed between the end of one sensor regeneration and the start of another sensor regeneration, may be defined as the sensor response time. The response time may not be a fixed time period but may vary based on vehicle operating conditions (e.g., engine load, speed), gas temperature and fuel quality etc. which affect soot level, soot conductivity etc. in the exhaust. The difference in response time may be partially or totally compensated by the controller 12.

In one example, due to impingement of large soot particles and/or water droplets on the electrodes 220, the soot accumulation signal may be noisy, e.g., having large soot flake, dust particles, etc. For example, there may be sudden dips and spikes in the signal (that is, higher than threshold change in data). This can lead to erroneous estimation of PM sensor 200 response time. During such conditions, the actual response time may be disregarded and instead a predicted response time may be used for updating an average response time and determining soot concentration in the exhaust gas. In particular, a part of the soot accumulation signal (current recorded by device 226) that is free of noise (such as signal accumulated during steady state operation of the vehicle) may be used to predict the PM sensor 200 response time even before the soot load of the PM sensor element 254 reaches the threshold. A quadratic equation may be fitted to the soot accumulation plot (electrical current) obtained during steady state operation and the response time may be predicted by extrapolating the curve fit even before the actual signal reaches the threshold value. Alternatively, the linear term of the quadratic fit may also be used to estimate the sensor rate of accumulation of soot and thus exhaust gas PM concentration. The soot load and PM sensor response time estimates, as obtained from extrapolation of the curve fitted to the accumulation plot and the linear term of the fit, may be averaged to get a more accurate estimation of the soot concentration in exhaust gas. During a first condition, responsive to the curve fit being higher than a threshold (value of coefficient of determination, $R^2$), soot sensor regeneration may be initiated at a first time; and during a second condition, responsive to the curve fit being lower than the threshold, soot sensor regeneration may be initiated at a second time, later than the first time. The first time may be a time when the curve fit exceeds the threshold, and the second time includes a threshold duration elapsed since completion of an immediately preceding regeneration of the sensor. On completion of prediction of response time, the response time may be stored and the PM sensor may be regenerated and reset rather than waiting for the threshold.

In this way, by monitoring the deposition rate and/or the response time of the PM sensor located downstream of the particulate filter, it may be possible to diagnose leaks in the particulate filter located upstream of the PM sensor even if the sensor data is noisy. Similarly, by monitoring the PM sensor located upstream of the particulate filter it is possible to determine the rate of PM deposition on the PF.

FIGS. 1 and 2 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example.

FIG. 3 illustrates an example method 300 for predicting a response time of the particulate matter (PM) sensor coupled to an engine exhaust passage downstream of a particulate filter based on soot accumulation signal collected during steady-state vehicle operation. Instructions for carrying out method 300 and the rest of the methods included herein may be executed by a controller (or controllers) based on instructions stored on a memory of the controller and in conjunction with signals received from sensors of the engine system, such as the sensors described above with reference to FIGS. 1 and 2. The controller may employ engine actuators of the engine system to adjust engine operation, according to the methods described below. Prior to the start of the method, there may be sensor regeneration, sensor protection operation, diagnostic checks and calibration.

At 302, the routine includes determining if a particulate matter regeneration has been completed. During PM sensor regeneration, a voltage is applied to a circuit (such as the second electric circuit 259 in FIG. 2) thermally coupled to the sensor element from a voltage source coupled to the circuit. The controller may actuate a switch (such as switch 232 in FIG. 2) coupled to the circuit to a closed position thereby completing the circuit. Upon closing the switch, the circuit is completed and electric current is flowed through the circuit, heating up a heating element (such as heating element 218 in FIG. 2) which is coupled to the sensor element. Typically, temperature higher than 600° C. is required for regenerating a non-catalytic surface. The heat from the heating element cleans the sensor element, in particular the electrodes, by burning off the soot accumulated on them. Subsequently, when the sensor electrodes are sufficiently clean (such as when the electric current output by the sensor has dropped), the controller may open the switch to stop heating the heating element. In one example, the switch may be maintained in the closed position for a pre-determined amount of time that is required to burn off a soot load accumulated corresponding to the threshold soot accumulation signal strength. In another example, the decrease in soot load on the sensor element may be estimated by monitoring a change (drop) in electric current and in response to the electric current value reaching a lower threshold, the switch may be actuated to the open position. By regenerating the PM sensor, it may be returned to a condition (e.g., completed unloaded or partially loaded condition) more suitable for further collection of exhaust soot. It will be appreciated that when the sensor is regenerating, no sensor data is collected. If regeneration is not completed, at 303, the routine includes continuing to complete sensor regeneration by maintaining the circuit closed (or maintaining a pulse width modulation).

If the sensor regeneration is complete, it may be inferred that the sensor is ready for soot and data collection. Accordingly, at 304, the controller may initiate collection of soot accumulation data from the PM sensor. This includes accumulating electric current measurements in the PM sensor. The electric current measurements may be carried out by a device (such as the device 226 in FIG. 2) which is part of an electric circuit (such as the first electric circuit 258 in FIG. 2) of the particulate matter (PM) sensor. Due to the accumulation of soot particles on a PM sensor element (such as the sensor element 254 in FIG. 2), an increase in electric current signal passing through a circuit (such as circuit 258 in FIG. 2) coupled to the sensor element may be observed. The strength of the soot accumulation signal is directly proportional to the soot load of PM particles adhered onto the sensor element and the signal strength may continuously increase as the soot load on the PM sensor element increases. The strength of the soot accumulation load signal is the electric signal measured by a micro-ammeter (such as the micro-ammeter 226 in FIG. 2). The electric signal is a gain that depends on a protection tube (such as the protection tube 250 in FIG. 2), electrode design of the PM sensor, voltage, residual soot not burned in previous regeneration, flow, temperature and other factors. The rate of change of current is also a function of the rate of soot accumulation.

At 306, a timer may be initiated at the same time as the initiation of signal collection so as to enable the controller to record a time elapsed since the onset of soot accumulation signal collection at the PM sensor (termed as $T_0$). This may be a time immediately following the previous sensor regeneration. PM sensor data collected immediately following a sensor reset may be used for calibration or self-diagnosis of the sensor. There is a time period where the current is close to or at zero, where the soot particles have not yet accumulated on the electrodes and this time may be termed as the dead time of the sensor. In one example, the time required to reach a signal strength of 1 µA threshold may be the dead time of the PM sensor. Starting from the end of sensor regeneration and after long enough time has elapsed for the electrodes to cool (from $T_0$), the time required ($T_{ref}$) to reach the threshold value of soot loading at which PM sensor regeneration may be required is the response time of the sensor. Alternatively, the dead time may be an amount of time that is not used to calculate the response time. Response time may not be a fixed time period for a particular sensor but may vary based on vehicle operating conditions (e.g. engine load, speed), fuel quality and PF efficiency which affect soot level in the exhaust. Due to emissions regulations, PM sensors are required to measure PM emission and gage PF efficiency at least once within one emission test cycle (such as a federal test procedure cycle, WHTC, NEDC etc.). Also, regulations require a PM measurement in a certain fraction of vehicle drive cycles; therefore a faster measurement will raise the completion ratio.

At 308, the soot accumulation signal may be retrieved. For example, the controller may record an increase in signal strength with increase in soot accumulation on the sensor element over time. Once the soot accumulation signal has been determined, a signal vs. time plot may be recorded. At 310, the routine includes determining if the signal to noise ratio in the collected signal is higher than a threshold value. High signal to noise ratio corresponds to smooth data collection such as during steady state operation of the vehicle. Such low noise data may be used to reliably predict response time of the PM sensor. On completion of prediction, the sensor may be regenerated and reset without having to wait for the measured and/or predicted response time. On completion of a regeneration event, data collection for the next dataset may commence thereby making it possible to include more number of sensor response time measurements per drive cycle. Low signal to noise ratio corresponds to noisy data collected either during transient engine operations or during impingement of large particulate matter, water droplets, etc., on the PM sensor. It is not possible to predict response time from such noisy signal.

If it is determined that the signal to noise ratio is lower than the threshold value, at 312, the routine includes determining if the time duration since onset of signal collection (from time $T_0$) is higher than a threshold time. In one example, this threshold time may be a pre-determined duration. In another example, the threshold time may depend on the average response time collected over one or more drive cycles. Therefore every time the average response time is updated after a successful response time measurement and/or prediction, the threshold time may also be updated. If it is determined that the duration since the onset of signal collection (from time $T_0$) is lower than the threshold time, at 318, collection of soot accumulation signal may be continued. PM sensor may not be regenerated at this time. If it is determined at 312 that the duration since the onset of signal collection is higher than the threshold time, at 314, the PM sensor may be regenerated and reset. Signal may not be collected during the regeneration and reset of the sensor. Following the sensor regeneration, signal collection may be initiated for the next dataset (e.g., the routine of FIG. 3 may run again). Since the last captured dataset comprises noisy data, this data may not be used to predict and update response time of the sensor.

If at 310 it is determined that the signal to noise ratio is high, at 316, the routine includes determining if the vehicle is operating in a steady-state condition. Under steady-state operation, engine operating parameters (such as engine speed, load, temperature etc.) may remain stable and may not fluctuate significantly. Also, during steady state operation of the vehicle, the vehicle speed may not change frequently. Under such conditions, soot is accumulated on the PM sensor at a relatively constant rate and the accumulation plot may show a monotonic increase in soot accumulation signal strength corresponding to the accumulated soot load. Also during this period, noise (spikes and dips) is not expected in the soot accumulation signal.

If it is determined that the vehicle is not being operated in a steady state condition, at 318, collection of soot accumulation signal may be continued. In one example, at 319, the routine includes determining if the current (signal) strength is higher than a threshold value of current. If it is determined that the signal strength is higher than a threshold, the routine may move to step 326, wherein, the timer recording the time elapsed since the onset of signal accumulation (from step 306) may be stopped. If it is determined that the signal strength is lower than the threshold, the electric current measurements may be continued to be carried on corresponding to the accumulation of soot load on the PM sensor elements. If at 316, it is determined that the vehicle is operating in steady state, at 320, a portion of the total signal accumulated (thus far) during steady state conditions may be used for prediction of a sensor response time even before the accumulated signal reaches the pre-determined regeneration threshold. A polynomial (e.g., quadratic) equation may be used to fit a plot generated from soot accumulation data collected thus far during the steady state operation of the vehicle. Data collected during non-steady state operation is rejected from the curve fitting and not used to fit the plot. The coefficients of the quadratic equation may be computed in order to provide a close fit to the soot accumulation plot. The quality of the fit may be determined by the coefficient of determination ($R^2$) of the plot. The closer the value of $R^2$ ($0<R^2<1$) to 1, the better the fit.

At 322, the routine includes determining if the value of $R^2$ for the quadratic curve fit is higher than a threshold value. The threshold value may correspond to a quality of fit required for reliable prediction of response time based on the curve fitted to the soot accumulation plot. In one example, the threshold value of $R^2$ is 0.7. If it is determined that the value of $R^2$ is lower than the threshold value, at 324, the co-efficient of the quadratic equation used to fit the soot accumulation plot may be changed in order to achieve a better fit (higher value of $R^2$). The co-efficient of the quadratic equation used in the curve fit may be varied to achieve a fit with a higher than threshold value of $R^2$ is obtained.

If it is determined that the value of $R^2$ is higher than the threshold, at 326, the timer recording the time elapsed since the onset of signal accumulation (from step 306) may be stopped. The signal (of high signal to noise ratio) collected during this time period may be used to predict the response time of the PM sensor.

At 328, the response time of the PM sensor may be predicted from the curve fit using one or more approaches. In a first example approach, at 330, the curve fit may be extrapolated to determine the time ($T_{ref}$) corresponding to a pre-determined threshold signal strength. In this way, using the extrapolated curve fit, it may be possible to predict the response time (time required to reach the threshold) of the PM sensor in advance (that is, before a duration corresponding to the actual response time elapses). As an example, the threshold signal strength may be <12 µA of electric current based on the projected or modeled rate of soot load reaching the PM sensor at the future extrapolated time ($T_{ref}$). In a second example approach, at 332, the linear slope term of the fitted polynomial may be used to estimate the average soot load accumulated on the PM sensor over a period of time. During steady state operating conditions, soot accumulation is uniform, therefore the exhaust soot concentration may be inferred from the estimated average soot load rate increase as measured by the current rate increase. The soot load rate can be converted to the predicted response time. In addition, in a third example approach, the time as determined when actual current (signal) strength reaches a threshold current (at step 319) may be recorded as the $T_{ref}$.

At 334, on completion of a successful curve fitting procedure to determine the time (Tref) to reach the threshold signal strength (or via an actual $T_{ref}$ measurement), it is no longer necessary to accumulate signals in the current data-cycle. Therefore at this time, the PM sensor may be regenerated and reset independent of the current signal strength and without waiting for the actual and/or predicted response time. During PM sensor regeneration, a heating element coupled to the sensor element is heated using electricity thereby causing the soot accumulated on the sensor element to be burnt off. In case the curve fit is not above a first threshold (value of $R^2$ below a first threshold), the controller may initiate regeneration of the sensor responsive to the electric current signal (output of a first electric circuit) exceeding a second threshold value of current (different from the first threshold).

At 336, the time required to reach the threshold signal strength may be recorded and used to calculate the response time ($T_{ref}-T_0$) for the PM sensor. In one example, the time estimated by each of the approaches (mentioned in steps 319, 330 and 332 respectively) to reach the threshold signal strength may be used to obtain an average response time. For example, the average response time may be a statistical or weighted average of the response times determined via the two example approaches. By predicting an average response time using at least two techniques, it is possible to improve the accuracy of the response time used for measuring PM concentration and tailpipe emissions. At 338, the average response time collected over the drive cycle may be updated with the last determined (predicted) response time. Alternatively, a calculation of soot concentration and/or flux may be carried out from the estimated response time and then an average soot concentration and/or flux may be calculated from a plurality of measurements during the drive cycle.

At 340, the efficiency of the PF may be measured from the average response time ($T_{ref}-T_0$) of a PM sensor coupled to the exhaust passage downstream of the PF. Also, by using other sensor data and computer models, effective percent function of the PF may be inferred. In case of a PM sensor coupled to the exhaust passage upstream of the PF, the response time may be used to infer the average soot concentration in the gas feeding into the PF. Soot accumulated on the PF over the response time span is directly proportional to the soot load accumulated on the PM sensor upstream of the PF. As the soot load on the PF reaches a pre-defined threshold load, the filter is required to be regenerated (cleaned). Soot load of the exhaust particulate matter filter may be predicted based partly on the response time of the exhaust soot sensor positioned upstream of the exhaust particulate matter filter, and the exhaust particulate matter filter may be regenerated based on the predicted soot load of the exhaust particulate matter filter. PM filter regeneration may then be scheduled based on the mass of PM estimated to be deposited within the PF and the regeneration of the Pm sensor. In this way the method includes estimating one or more of an exhaust soot concentration and an exhaust soot flow rate proportional to the predicted sensor output. The method further comprises diagnosing a PF efficiency using upstream and downstream exhaust soot sensors. In one example, estimation of PF efficiency may not be based on the PM sensor coupled upstream of the PF, and the PM sensor coupled downstream of the PF may alone be used along with inferred soot concentration estimates obtained from models and other sensors coupled to the controller. The efficiency estimation may be based on the updated average response time including indicating filter degradation (leak) based on the updated average response time being lower than a threshold duration and an estimated soot flux at the filter inlet. The soot sensor positioned downstream of the PF may also be used to estimate the efficiency of the PF based on a comparison of the soot flux at the filter outlet to the soot flux at the filter inlet (as measured or estimated). PM sensors present both upstream and downstream of the particulate filter provide an accurate estimation of soot concentration at the point where the sampling is done for the respective sensor. By following this method, there is less chance of losing a measurement cycle due to spikes of current. Once the sensor is reset it may be recalibrated and soot accumulation on the sensor may be resumed for the next dataset.

In the above example, the response time is predicted based on soot sensor data collected during steady-state conditions, irrespective of whether soot sensor signal transients (e.g. spikes or dips) occur. In other words, steady state data is always used, as a default, for predicting the response time, and once the predicted response time is determined, soot sensor may be regenerated and reset. This method further includes estimating one or more of an exhaust soot concentration and an exhaust soot flow rate from the predicted sensor response time, and diagnosing particulate matter emission from the vehicle based on the one or more of an exhaust soot concentration and an exhaust soot flow rate. In this way, by utilizing a larger amount of sensor signal accumulated over a drive cycle (and discarding a smaller amount of the accumulated signals), the likelihood of completing PM sensor soot concentration measurement at least once within a given emission test cycle (such as a federal test procedure cycle) is increased. Also, a more accurate response time may be used for sensor PM measurement (e.g., in terms of mg/mile PM) in place of an actual response time which may be not be suitable for the particular data set because of under prediction or over prediction of soot particle load on the electrodes It will be appreciated that while the described method of prediction of response time from a quadratic fit to a part of accumulated signal is described with reference to the output of a soot sensor signal, it may be similarly utilized for a plurality of other sensors present in a vehicle or for modeled accumulated signal (virtual sensors) in the controller. Example of other sensors with an increasing or decreasing signal where the above described method may be used include backpressure sensor, temperature sensor (in a known increasing heat up mode), fuel tank purge pressure sensor, speed sensors (in known accelerating or decelerating mode), air/fuel ratio sensor etc.

FIG. 4 shows an example soot accumulation plot 400 of a particulate matter (PM) sensor signal with a curve fitted to the accumulation plot. The horizontal (x-axis) denotes time in seconds and the y-axis shows the soot accumulation signal strength (magnitude of electric current in μA passing through a sensor element) in a PM sensor. The soot accumulation signal strength is directly proportional to the amount of soot deposited on the sensor element. During operation of the vehicle, soot may accumulate on the PM sensor coupled to the exhaust passage upstream and/or downstream of a particulate filter (PF). As such, PM sensors need to be regenerated and reset once the soot accumulation signal strength reaches a threshold value. The time required for a sensor signal to reach the threshold value is known as the response time of the sensor. In order to meet emissions regulations, PM sensors are required to be intermittently regenerated and reset (e.g., at least once within each emission test cycle). The vertical markers t1-t4 identify significant times during soot accumulation and PM sensor regeneration. The horizontal line I1 denotes the magnitude of current (in μA) corresponding to the threshold signal strength at which the sensor may be regenerated and reset.

Plot 402 shows an aggregated output of soot sensor (soot accumulation data) over time. A first portion of the data collected from t0 to t1 may be used for calibration of the sensor. The time period from t0 to t1 during which the calibration takes place may be termed as the dead-time of the sensor. In one example, the time required to reach a signal strength of 1 μA may be the dead time of the PM sensor. In this example, time t1 denotes the end of dead time of the sensor. The dead time may be envisioned as the time where soot particles accumulate but do not bridge the gap between the electrode pair. The dead time shown in this example is not to scale and may be of longer duration (compared to time between t0 and t1).

Between time t1 and t2, soot load data collected may show a monotonic increase in magnitude of electric current corresponding to the accumulated soot load. During this time period, since the vehicle is operating under steady state conditions, the soot accumulation signal may be substantially noise-free (electric current is within an expected range without sudden spikes and/or dips).

At time t3, there is a sudden increase in noise in the accumulated data of this example. Noisy signal may occur during transient engine operation, from electromagnetic compatibility (EMC) noise and/or due to large soot particles, dust particles, or water droplets impinging on the sensor element. Such noisy data may be considered erroneous and may not reflect the actual soot load on the sensor. In this example, the sudden spike in PM sensor signal (e.g., to higher than a regeneration level) may not have a corresponding spike in PM loading on the sensor. As such, if the PM sensor were regenerated based on the sudden increase, the sensor may be regenerated prematurely. Consequently, the controller may disregard the signal and not utilize the accumulated data for determination of a sensor response time. If the controller uses the response time from the actual data (t3−t1), it will result in an erroneous calculation of high soot concentration in the exhaust.

In order to enable a significant portion of the accumulated data to be used for determination of the sensor's response time, and to reduce the reliance on a predetermined average response time, the controller may rely on the data collected at the sensor during steady state operation (that is, between t1 and t3, and before occurrence of the erroneous signal at t3) for predicting a response time. The predicted response time may then be used for sensor regeneration. The determination of vehicle steady state operation may be based at least one of engine operating conditions and current signal (line 402).

It is observed from plot 402 that a part of the data, between time t1 and t3 is free from any noise. This region of the plot (between time t1 and t3) is termed as series 1. This data in series 1 may correspond to uniform soot accumulation during steady state operation of the vehicle. The soot accumulation data collected during such steady state operation (such as between time t1 and t3) may be effectively used for prediction of sensor response time even before the response time is reached. A quadratic equation may be fitted to the data in series 1 to obtain the curve fit 406. The value for $R^2$ for the curve fit 406 is compared to the threshold value for $R^2$. In this example, the value for $R^2$ for the curve fit 406 is higher than the threshold value and therefore the fit 406 may be utilized for prediction of sensor response time. The fit 406 may be extrapolated to determine the point of intersection between fit 406 and line I1. The time corresponding to this intersection point (t4) corresponds to the predicted response time of the PM sensor. As such, if the vehicle continued to operate under steady state conditions without, for instance, impingement of large soot particles and/or water droplets on the PM sensor, the soot accumulation signal would be expected to reach the threshold value signal strength (line I1) at time t4. Thus, upon determination (prediction) of response time, the sensor may be regenerated and reset at t3 independent of the actual signal strength of the sensor (that is, independent of whether the actual signal is higher or lower than the regeneration threshold) and the predicted response time. Following the regeneration and reset of the sensor the next set of data collection may be initiated. In this way by early regeneration of the sensor, it is possible to maximize the number of response time measurements, soot load estimation and sensor regenerations within a drive cycle (as per federal regulations).

In addition the linear slope term of the curve fit 406 may be used to estimate the average soot load accumulated on the PM sensor between time t1 and t3. During steady state operating conditions, soot accumulation is uniform, therefore the predicted response time (t440) may be estimated from the rate of average soot deposition between time t1 and t3. Other factors (e.g., engine speed, engine load, temperature, exhaust flow) may be required to be taken into account while predicting the response time from the linear slope term of the curve fit. Response time estimated by the two techniques (extrapolation of curve fit and use of linear slope term of curve fit) may be used to obtain predicted response time (t4–t0). In this way by using average response time as predicted by two techniques, it is possible improve the accuracy of the response time used for PM sensor regeneration.

If the entire data set (post time t1) including the noisy signal is taken into account for prediction of response time, it may not be possible to reliably predict response time using a curve-fitting approach. As an example, the entire set of data collected after time t1, herein termed as data series 2, may be used for predicting the response time. Specifically, the controller may fit a curve to data series 2 (solid dots). Dotted line 404 shows an example best square curve fitted to the series 2 data. The quality of the fit of curve may be determined by comparing the coefficient of determination ($R^2$) value of the curve fit to a pre-determined threshold value. In this example, the $R^2$ of the curve fit 404 may be lower than threshold value for $R^2$. This may be due to the fact that a large part of the data in series 2 is noisy and may not be suitable for use in response time prediction. Due to the low quality of the curve fit 404, it may not utilized for estimation of sensor response time. Also, due to the unavailability of a reliable response time, usage of this technique will give rise to inaccuracies in particulate filter (PF) soot load estimation.

In one example, if the actual response time is used for regeneration and the soot accumulation is slow (such as during instances of a downward spike during a transient engine condition), the response time will be too high and a PM sensor (coupled downstream of the PF) would not be able to detect an occurrence of a degraded PF. In another example, if the actual response time is shorter (such as during instances of an upward spike or noise during a transient engine condition), efficiency estimation of the PM sensor (coupled downstream of the PF) would be erroneous leading to false detection of a non-degraded PF. Therefore, upon availability of noise-free steady state signal, it is advantageous to use a predicted response time for determination of PM sensor efficiency and PF performance.

In still further examples, the controller may also schedule PM sensor regeneration based on current and future driving conditions. For example, the controller may rely on data accrued from vehicle navigation systems (e.g., on-board GPS device), vehicle-to-vehicle (V2V) communication systems, etc., to predict future driving conditions. Based on the predicted response time and further based on the predicted driving conditions, the controller may schedule PM sensor regeneration early and calculate the PM concentration. As an example, the controller of a vehicle having a navigation (e.g., GPS) system may determine that the vehicle is about to enter a highway with a 65 MPH speed limit (e.g., based on a travel route planned by the vehicle operator and entered into the navigation system). Herein, the controller may use soot accumulation signal collected during vehicle operation at 40 MPH to predict the response time (corresponding to 40 MPH vehicle speed) for the soot sensor without having to wait for the actual signal strength to reach the threshold value. On completion of response time prediction, the PM sensor may be regenerated and reset and the controller may make a note that this soot accumulation set was carried out at 40 MPH speed limit. A new set of data may be collected (after sensor regeneration) corresponding to vehicle operation at 65 MPH. By comparing different sets of response times corresponding to different vehicle speeds, it is possible to differentiate and monitor particulate filter (PF) health at multiple vehicle speeds and corresponding operating conditions. It is also possible to avoid collecting noisy data by determining future possibilities of transient engine conditions, predicting a response time from the steady state data and regenerating and resetting the sensor during the transient engine operation. The controller may also populate and update a look-up table of response times stored in the controller's memory as a function of average vehicle speed. The controller may then use the series data behavior learned during vehicle steady-state operation at 65 MPH the next time the vehicle is operating at 65 MPH (or on a section of road having a 65 MPH speed limit) and use the information to schedule early sensor regeneration if transients occur that disrupt the actual signal.

This method not only improves the chance of completion of response time determination and sensor regeneration within short drive cycles but also improves the accuracy of the average response time calculated from a higher number of repose time signal accumulations within a drive cycle.

Figure 5:
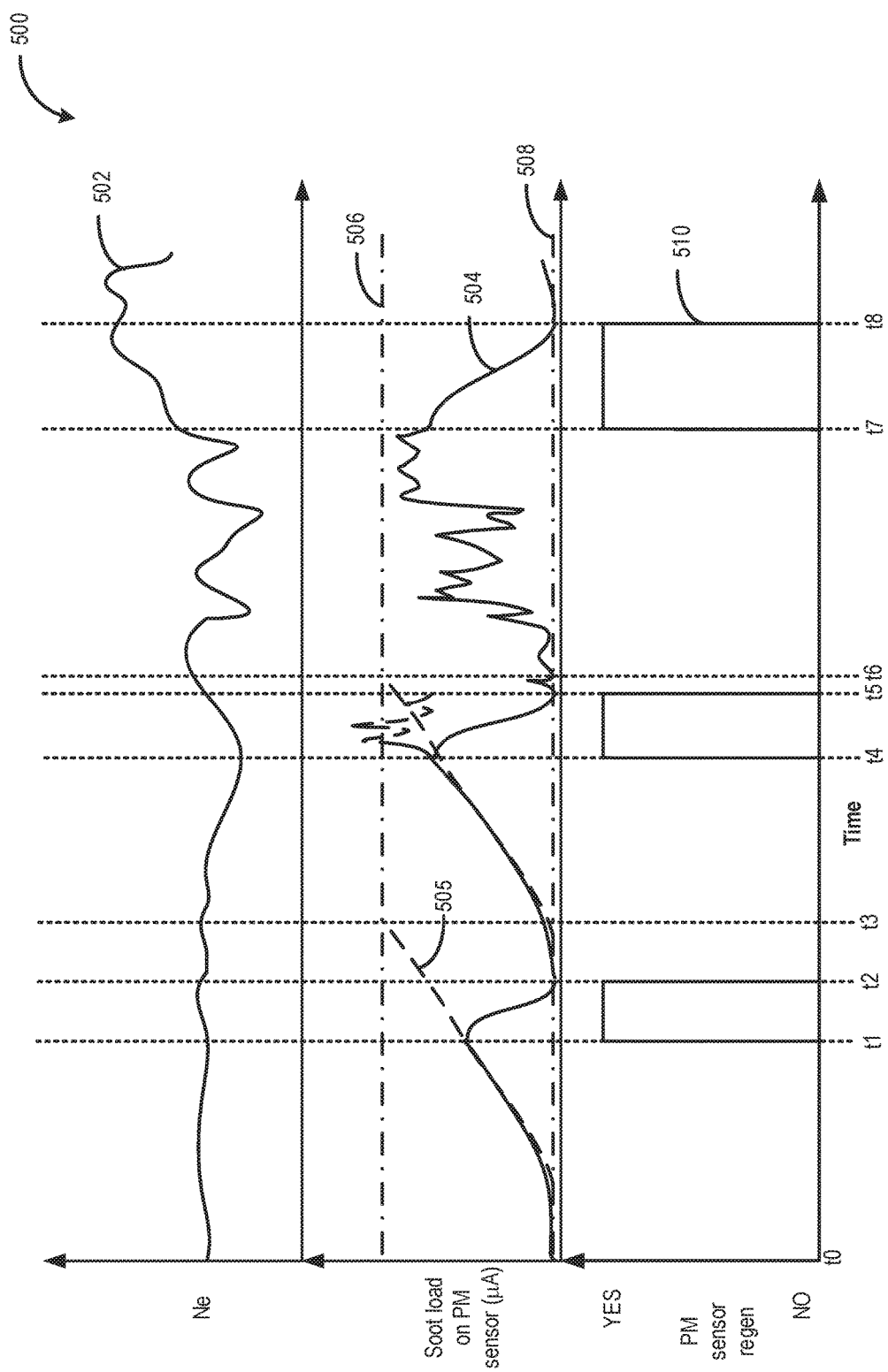
FIG. 5 shows an example regeneration of a PM sensor based on measured and predicted response times.

FIG. 5 shows an example operating sequence 500 illustrating regeneration of a particulate matter (PM) sensor based on measured and predicted response times. The horizontal (x-axis) denotes time and the vertical markers t0-t8 identify significant times for sensor regeneration. The first plot from the top shows variation in engine speed (line 502) over time. The second plot (line 504) shows the soot load accumulation on a sensor element of the PM sensor over time. The soot load is directly proportional to the PM sensor soot accumulation electric current signal measured in μA. The first threshold soot load at which the PM sensor is required to be regenerated and reset in shown by dotted line 506. The second (lower) soot load at which the PM sensor element may be regarded as clean is shown by dotted line 508. The second threshold may be zero or a small value of electric current (<1 μA). The quadratic curve fitted to soot accumulation signal collected during steady state operation of the vehicle is shown by dotted line 505. The third and final plot, 510, depicts PM sensor regeneration.

Time t0 may correspond to the end of a PM sensor regeneration and reset event followed by sensor calibration. Prior to time t1, the engine is operated at steady state conditions with no significant variation in engine speed over time. During this time, vehicle operating parameters such as vehicle speed, engine load, engine temperature etc., may not fluctuate significantly. Due to the steady state operation of the engine, soot may accumulate on the PM sensor at a relatively constant rate. Electric current passing through a circuit coupled to the sensor element is proportional to the soot load accumulated on the PM sensor and consequently the accumulation plot (line 504) may show a monotonic increase in magnitude of electric current corresponding to the accumulated soot load. During this time period, the soot accumulation signal may be substantially noise-free (electric current is within an expected range without sudden spikes and/or dips). Since the vehicle is operating under steady state conditions, a quadratic curve (dotted line 505) may be fitted to the soot accumulation plot prior to time t1. From the curve fit (line 505), the time required for the soot load to reach the threshold soot load at which sensor regeneration may be carried out (sensor response time) may be predicted. Response time prediction may be carried out either by extrapolating the curve fit to obtain the time at which soot load may reach the threshold load or by utilizing the linear slope term of the quadratic fit. In this example, the time at which the soot load is predicted to reach the threshold 506 is at t3. Therefore using the data collected during steady state engine operation (noise-free signal) prior to time t1, the response time (t3−t0) may be predicted at time t1.

As such, prior to t1, prior to prediction of response time, a switch on an electric circuit coupled to the PM sensor is held open and the PM sensor does not regenerate. If the switch is in the open state, the circuit is incomplete and there is no flow of current through it, whereas, when the switch is in the closed state the electric circuit coupled to the PM sensor is complete and current flows through it. Due to passage of current through the electric circuit, a heating element within the PM sensor may get heated causing the soot accumulated on the sensor element to be burnt off thereby cleaning the sensor element.

At time t1, upon completion of response time prediction, the sensor may be regenerated even before the soot load reaches the threshold 506. At this time, the controller may send a signal to actuate the switch of the electric circuit coupled to the PM sensor to the closed position. Once the circuit is complete, the sensor element is heated by the electricity passing through the circuit initiating PM sensor regeneration. During the regeneration process, the soot load on the PM sensor may reduce steadily as inferred from the decrease in soot accumulation signal (electric current) strength between time t1 and t2. During regeneration, the switch may be maintained in the closed position for a pre-determined amount of time that is required to burn off a soot load amount corresponding to the threshold load 506. Alternatively, the reduction in soot load on the sensor element may be estimated by monitoring the decrease in electric current and in response to the electric current value reaching a second lower threshold 508, the switch may be actuated to open position. Once the regeneration process is complete, at time t2, the sensor may be reset and a new set of soot accumulation signals may be collected. Once the sensor is reset, the sensor may be required to be calibrated. Sensor signal is not accumulated during the regeneration process.

Between time t2 and t4, the vehicle continues to operate at steady state conditions and correspondingly the soot load on the PM sensor may increase monotonically. Similar to the last soot accumulation cycle, a quadratic equation may be fitted to the to the soot accumulation plot between time t3 and t4 (ignoring the dead-time between time t2 and t3). PM sensor response time for this set of soot accumulation may be predicted from the curve fit to the noise-free signal collected during steady state operation between time t3 and t4. Based on the curve fit, it may be predicted that the PM sensor soot load would reach the first threshold load 506 at time t6. Upon completion of response time prediction, the sensor may be regenerated at time t4 even before the soot load in this dataset reaches the threshold 506. The sensor may be regenerated and reset between time t4 and t5. During the regeneration process, the switch of the electric circuit is held in the closed position. Once the soot load reduces to the second threshold 508, at time t5, the regeneration process may be suspended by actuating the switch of the electric circuit to the open position thereby preventing current flow in the circuit. After the regeneration of the PM sensor, the sensor may be reset to enable soot accumulation. The time required for sensor regeneration may not be equal for every dataset but may depend on the level of soot accumulated on the sensor. The higher the soot load, the longer it takes to be burnt off.

In this example, during sensor regeneration, between time t4 and t5, if signal collection would have been continued, increased noise level would have been detected in the soot accumulation signal (as shown as the hypothetical dotted line under circumstances that the PM sensor regeneration has not been initiated). Such noisy signal may occur due to impingement of large soot particles and/or water droplets on to the sensor elements even during smooth engine operations. Due to the erroneous signal, soot accumulation data collected between time t4 and t5 may not have been reliable for estimation of sensor response time. In this way, by utilizing a signal accumulated during steady state conditions, PM sensor response time prediction and regeneration can be carried out even when the overall signal is noisy.

In this example, between time t5 and t7, the vehicle operation may be transient (not steady). This may be due to conditions such as increased road roughness, high engine load etc. Due to unsteady operation, there is significant variation in engine speed during this time period. Also during this period, the soot load accumulation on the PM sensor is not uniform. Due to the lack of steady vehicle operation and uniform soot deposition, during this time it is not possible to fit a quadratic equation to any part of the soot accumulation plot. However, reliance on the erroneous data for sensor response time deduction may also lead to inefficient sensor regeneration. Under such circumstances, a pre-determined value of sensor response time may be utilized for sensor regeneration. Previous accurate measures and predictions of sensor response times may be used in determining the pre-determined value. Each time a response time is successfully predicted, the data is taken into account towards updating an average response time. Also, there may be a plurality of pre-determined response times based on corresponding vehicle operating conditions. As an example, there may be a set of learned average response times corresponding to different vehicle speeds or engine speeds. After the passage of the pre-determined response time, at time t7, it may be expected that the soot load on the PM sensor is close to the first threshold soot load 506.

Again, between time t7 and t8, the PM sensor regeneration event is carried out based on the pre-determined response time. The regeneration event is completed in response to the indication that at time t8, the soot load has reduced to the second threshold 508. After completion of the regeneration event, the PM sensor may be reset. After time t8, soot may continue to deposit on the PM sensor and the sensor may be further regenerated and reset either upon completion of a response time prediction or upon passage of a pre-determined response time in the absence of steady state data. In this way a large part of the accumulated soot load signal may be utilized for prediction of response time which may be further utilized to estimate soot concentration in the exhaust gas, PF functionality and PM sensor efficiency. In addition, by conducting early regenerations (without waiting for actual or predicted response time) it is possible to for an engine controller to collect a maximum number of sensor response time signals per drive cycle (to meet federal emission standards). It may be noted that FIG. 5 shows three possible examples and does not represent all possible signal scenarios that may occur in relation to soot accumulation on PM sensor.

An example method for an engine comprises collecting exhaust soot sensor data during engine operation while sensor noise is lower than a threshold; fitting a time-based curve to the collected data; predicting a sensor response time based on the curve fit; and in response to the curve fit being higher than a threshold, regenerating the soot sensor independent of a soot load of the sensor. Any of the preceding example, additionally or optionally further comprises updating an average response time of the sensor based on the predicted sensor response time. Any or all of the preceding example, additionally or optionally further comprises diagnosing a particulate matter filter located one of upstream and downstream of the exhaust soot sensor based on the updated average response time and indicating filter degradation based on the updated average response time being lower than a threshold duration. In any or all of the preceding examples, additionally or optionally, the regenerating independent of soot load includes regenerating independent of each of an actual sensor concentration and a predicted soot concentration. In any or all of the preceding examples, the curve fit is additionally or optionally a quadratic curve fit. Any of the preceding example, additionally or optionally further comprises estimating one or more of an exhaust soot concentration and an exhaust soot flow rate from the predicted sensor response time, and diagnosing particulate matter emission from the vehicle based on the one or more of an exhaust soot concentration and an exhaust soot flow rate. Any of the preceding example, additionally or optionally further comprises in response to the curve fit being lower than the threshold, adjusting a correlation coefficient of the curve fit. Any of the preceding example, additionally or optionally further comprises in response to the curve fit being lower than the threshold, regenerating the soot sensor based on the soot load of the sensor. In any or all of the preceding examples, additionally or optionally, the soot sensor is regenerated at an earlier time when the curve fit is higher than the threshold, and the soot sensor is regenerated at a later time when the curve fit is lower than the threshold. In any or all of the preceding examples, additionally or optionally, data collected when sensor noise is higher than the threshold is rejected from the curve fit. In any or all of the preceding examples, additionally or optionally, collecting exhaust soot sensor data during engine operation while sensor noise is lower than a threshold includes sensor data collected during steady-state operation, and wherein the predicting is based on data collected only during the steady-state operation.

Another example method for an engine comprises collecting data at an exhaust soot sensor; fitting a time-based curve to data collected during steady-state engine operation while sensor noise is lower than a threshold; predicting a sensor response time based on the curve fit; during a first condition, responsive to the curve fit being higher than a threshold, initiating soot sensor regeneration at a first time; and during a second condition, responsive to the curve fit being lower than the threshold, initiating soot sensor regeneration at a second time, later than the first time. In the preceding example, additionally or optionally, the first time is a time when the curve fit exceeds the threshold, and wherein the second time includes a threshold duration elapsed since completion of an immediately preceding regeneration event of the sensor. In any or all of the preceding examples, additionally or optionally, the threshold includes a value of a coefficient of determination for the curve fit. In any or all of the preceding examples, additionally or optionally, the soot sensor is positioned upstream of an exhaust particulate matter filter, the method further comprising regenerating the exhaust particulate matter filter based on the regenerating of the soot sensor, and measuring an efficiency of the exhaust particulate matter filter based on the regenerating of the filter. Any or all of the preceding examples, additionally or optionally further comprises during the first condition, discontinuing the collecting of data at the exhaust soot sensor at the first time; and during the second condition, discontinuing the collecting of data at the exhaust soot sensor at the second time. The response time of the soot sensor positioned upstream of the particulate filter (PF) may be used to calculate upstream soot concentration which may be further used to either determine PF regeneration time, or measure upstream soot flux as part of PF efficiency calculation by the controller. The response time of the soot sensor positioned downstream of the PF may be used to measure downstream soot flux as part of the PF efficiency calculation by the controller.

In yet another example an exhaust sensor system coupled to an engine system comprises a sensor element comprising an electrode pair and a heating element; a first electric circuit coupled to the sensor element; a second electric circuit coupled to the heating element; and a controller with computer readable instructions stored on non-transitory memory for: collecting sensor data based on an output of the first electric circuit; estimating a curve fit of the collected sensor data; initiating regeneration of the sensor responsive to the curve fit exceeding a threshold independent of actual sensor data; predicting a sensor response time based on the curve fit; averaging response time; and calculating exhaust soot values (e.g., soot concentration, particulate filter load and efficiency). In the preceding example, additionally or optionally, the first electric circuit includes a measuring device for recording a change in current in the electrode pair in response to soot accumulation on the sensor element and the second electric circuit includes a switch for initiating regeneration of the sensor element, and wherein the controller includes further instructions for updating an average sensor response time of the sensor system for a current drive cycle based on the predicted response time. In any or all of the preceding examples, additionally or optionally, the regeneration includes closing the switch of the second electric circuit and flowing electricity through the heating element. In any or all of the preceding examples, additionally or optionally, the threshold is a first threshold, and wherein the controller includes further instructions for: initiating regeneration of the sensor responsive to the output of the first electric circuit exceeding a second threshold, different from the first threshold when the curve fit does not exceed the first threshold.

In this way, even in the presence of noisy soot accumulation signal, it is possible to utilize signal accumulated during steady state conditions to predict a PM sensor regeneration schedule and to estimate soot concentration in the particulate matter filter. By using a larger portion of the accumulated signal for response time prediction (and discarding a smaller portion), on-board diagnostics may be completed within a drive cycle without reducing accuracy in the estimation of sensor response time. By predicting response time and regenerating the PM sensor upon completion of a prediction, collection of data for a new set may commence without having to wait for actual and/or predicted response time, therefore a maximum number of sensor response time signals may be collected per drive cycle. The technical effect of using a quadratic fit to the accumulation plot is that soot accumulation on the PM sensor may be estimated using at least two techniques (such as by extrapolating the quadratic fit to the first threshold for response time estimation and by using the linear term of the same fit to estimate soot concentration), thereby improving the accuracy of the sensor response time prediction. As a larger amount of the signal is utilized, the likelihood of achieving PM sensor regeneration and resetting at least once within one emission test cycle is increased. Also, by resetting accumulation once the corresponding response time has been predicted, more accumulations may be carried out within a given drive cycle. By improving accuracy of PM sensor located upstream of the particulate matter filter, regeneration of a PM filter can be scheduled more accurately, improving engine performance and fuel economy. By utilizing PM sensor's (located downstream of filter) estimate of soot concentration, PF efficiency may be estimated and a diagnostic monitor of the particulate matter filter's leak rate and efficiency may be completed.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

It will be further appreciated that the above technology may be applied to non-engine systems that generate soot particulate matter (PM) in a gaseous stream, such as combustion systems, power plants, home heating systems, etc., that may or may not have a particulate filler, and may need a PM flux or concentration measured. The above technology may be applied to any resistive sensor that detects PM in any stream of gas or liquid. The above technology may be applied to any accumulating signal from a sensor.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for a vehicle, comprising:
collecting exhaust soot sensor data with an exhaust soot sensor during engine operation while exhaust soot sensor noise is lower than a threshold;
fitting a time-based curve to the collected exhaust soot sensor data;
determining whether the curve fit is higher than a threshold, and in response to the curve fit being higher than the threshold, regenerating the exhaust soot sensor independent of a soot load on the exhaust soot sensor; and
updating an average response time of the exhaust soot sensor based on a predicted sensor response time that is predicted based on the curve fit.

2. The method of claim 1, further comprising diagnosing a particulate matter filter located upstream or downstream of the exhaust soot sensor based on the updated average response time and indicating filter degradation based on the updated average response time being lower than a threshold duration.

3. The method of claim 1, wherein the regenerating independent of soot load includes regenerating independent of each of an actual soot concentration and a predicted soot concentration.

4. The method of claim 1, wherein the curve fit is a quadratic curve fit.

5. The method of claim 1, further comprising estimating one or more of an exhaust soot concentration and an exhaust soot flow rate from a predicted sensor response time that is predicted based on the curve fit, and diagnosing particulate matter emission from the vehicle based on the one or more of the exhaust soot concentration and the exhaust soot flow rate.

6. The method of claim 1, further comprising, in response to determining that the curve fit is lower than the threshold, adjusting a coefficient of the curve fit.

7. The method of claim 1, further comprising, in response to determining that the curve fit is lower than the threshold, regenerating the exhaust soot sensor based on the soot load of the exhaust soot sensor.

8. The method of claim 7, wherein the exhaust soot sensor is regenerated at a first time when the curve fit is higher than the threshold, and the exhaust soot sensor is regenerated at a second time when the curve fit is lower than the threshold, the first time earlier than the second time.

9. The method of claim 1, wherein the exhaust soot sensor data collected when the exhaust soot sensor noise is higher than the threshold is rejected from the curve fit.

10. The method of claim 1, wherein collecting the exhaust soot sensor data during engine operation while the exhaust soot sensor noise is lower than the threshold includes collecting exhaust soot sensor data during steady-state operation, and wherein predicting is based on exhaust soot sensor data collected only during the steady-state operation.

11. A method for a vehicle engine, comprising:
collecting data with an exhaust soot sensor;
fitting a time-based curve to data collected with the exhaust soot sensor during steady-state engine operation while exhaust soot sensor noise is lower than a threshold;
responsive to the curve fit being higher than a threshold, initiating regeneration of the exhaust soot sensor at a first time; and
responsive to the curve fit being equal to or lower than the threshold, initiating regeneration of the exhaust soot sensor at a second time, later than the first time.

12. The method of claim 11, wherein the first time is a time when the curve fit exceeds the threshold, and wherein the second time includes a threshold duration having elapsed since completion of an immediately preceding regeneration event of the exhaust soot sensor.

13. The method of claim 11, wherein the threshold includes a value of a coefficient of determination for the curve fit.

14. The method of claim 11, wherein the exhaust soot sensor is positioned upstream of an exhaust particulate matter filter, the method further comprising regenerating the exhaust particulate matter filter based on the regenerating of the exhaust soot sensor, and measuring an efficiency of the exhaust particulate matter filter based on the regenerating of the exhaust particulate matter filter; wherein the exhaust soot sensor comprises an electrode pair and a heating element.

15. The method of claim 11, further comprising:
responsive to the curve fit being higher than the threshold, discontinuing the collecting of data with the exhaust soot sensor at the first time; and
responsive to the curve fit being equal to or lower than the threshold, discontinuing the collecting of data with the exhaust soot sensor at the second time.

16. An exhaust sensor system coupled to an engine comprising:
a sensor element positioned upstream or downstream of a particulate matter filter, the sensor element comprising an electrode pair and a heating element;
a first electric circuit coupled to the sensor element;
a second electric circuit coupled to the heating element; and
a controller with computer readable instructions stored on non-transitory memory for:
collecting sensor data based on an output of the first electric circuit;
estimating a curve fit of the collected sensor data;
initiating regeneration of the sensor element independent of actual sensor data representing an actual soot load of the sensor element responsive to the curve fit exceeding a first threshold; and
initiating regeneration of the sensor element responsive to the output of the first electric circuit exceeding a second threshold, different from the first threshold, responsive to the curve fit not exceeding the first threshold.

17. The system of claim 16, wherein the first electric circuit includes a measuring device for recording a change in current in the electrode pair in response to soot accumulation on the sensor element and the second electric circuit includes a switch for initiating regeneration of the sensor element, and wherein the controller includes further instructions for closing the switch of the second electric circuit and flowing electricity through the heating element to initiate the regeneration.

18. The system of claim 16, wherein the controller includes further instructions for:
updating an average sensor response time of the exhaust sensor system for a current drive cycle based on a predicted sensor response time that is predicted based on the curve fit, and wherein initiating regeneration of the sensor element independent of the actual sensor data representing the actual soot load of the sensor includes initiating regeneration of the sensor element independent of the actual soot load of the sensor element exceeding a threshold soot load.

* * * * *